(12) United States Patent
Dücker et al.

(10) Patent No.: US 6,872,558 B1
(45) Date of Patent: Mar. 29, 2005

(54) HEPARANASE-2 A MEMBER OF THE HEPARANASE PROTEIN FAMILY

(75) Inventors: Klaus Dücker, Darmstadt (DE); Christian Sirrenberg, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 122 days.

(21) Appl. No.: 10/088,676

(22) PCT Filed: Sep. 11, 2000

(86) PCT No.: PCT/EP00/08837

§ 371 (c)(1), (2), (4) Date: Mar. 21, 2002

(87) PCT Pub. No.: WO01/21814

PCT Pub. Date: Mar. 29, 2001

(30) Foreign Application Priority Data

Sep. 23, 1999 (EP) .............................. 99118805
Jul. 7, 2000 (EP) .............................. 00114649

(51) Int. Cl.⁷ ............................. C12N 9/00; C12N 9/24; C12N 1/12; C12N 15/00; C07H 21/04
(52) U.S. Cl. ............................. 435/200; 435/4; 435/6; 435/69.1; 435/183; 435/192; 435/252.3; 435/320.1; 435/325; 536/23.2; 536/23.4; 536/23.5; 530/350
(58) Field of Search .............................. 435/4, 6, 69.1, 435/183, 200, 209, 252.3, 320.1; 536/23.2, 23.5, 23.7; 530/350

(56) References Cited

U.S. PATENT DOCUMENTS 5,968,822 A * 10/1999 Pecker et al. ................ 435/325
6,461,848 B1 * 10/2002 Nakajima et al. ............ 435/209

FOREIGN PATENT DOCUMENTS

| WO | WO 99 11798 A | 3/1999 |
| WO | WO 99 21975 A | 5/1999 |
| WO | WO 99 43830 A | 9/1999 |
| WO | WO 200100643 A2 * | 1/2001 |

OTHER PUBLICATIONS

E. McKenzie et al., "Cloning and Expression Profiling of hpa2, a Novel Mammallan Heparanase Family Member," Biochemical and Biophysical Research Communications, vol. 276, No. 3, pp. 1170–1177, Oct. 5, 2000, XP002155087.

M.A. Kosir et al., "Degradation of Basement Membrane By Prostate Tumor Heparanase." Journal of Surgical Research, vol. 81, No. 1, pp. 42–47, Jan. 1999, XP002155606, Abstract p. 45, right–hand column, line 13–p.46, left–hand column, line 18.

M.A. Kosir et al., "Human Prostate Carcinoma Cells Produce Extracellular Heparanase," Journal of Surgical Research, vol. 67, No. 1, pp. 98–105, Jan. 1997, XP002155605, Abstract p. 102, right–hand column, line 23–p. 103, left–hand column, line 15.

R. Strausberg, "qg97h02.x1 Soares_NFL_T_GBC_S1 *Homo sapiens* cDNA clone IMAGE:1843155 3', mRNA sequence," Database EMBL 'Online! EMBL; ID A1222323, AC AC A1222323, Nov. 30, 1998, XP002155607.

* cited by examiner

*Primary Examiner*—Manjunath Rao
(74) *Attorney, Agent, or Firm*—Millen, White, Zelano & Branigan, P.C.

(57) ABSTRACT

Heparanase-2 polypeptides and polynucleotides and methods for producing such polypeptides by recombinant techniques are disclosed. Also disclosed are methods for utilizing heparanese-2 polypeptides and polynucleotides and diagnostic assays.

16 Claims, 2 Drawing Sheets

HEPARANASE-2 A MEMBER OF THE HEPARANASE PROTEIN FAMILY

FIELD OF THE INVENTION

Figure 1:
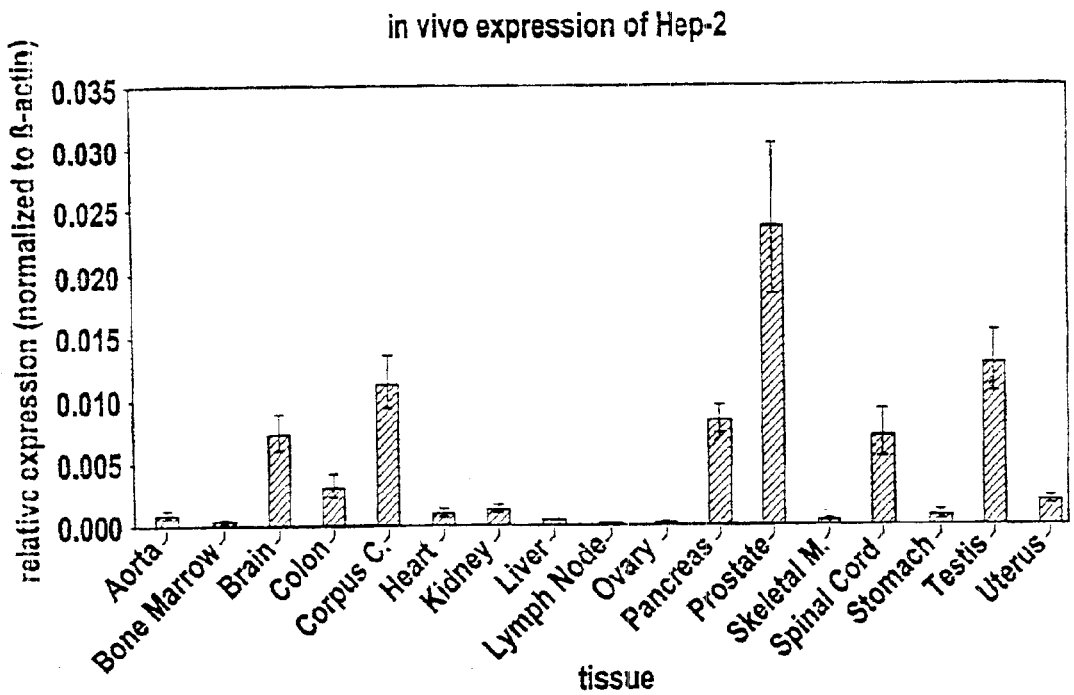
Figure 2:
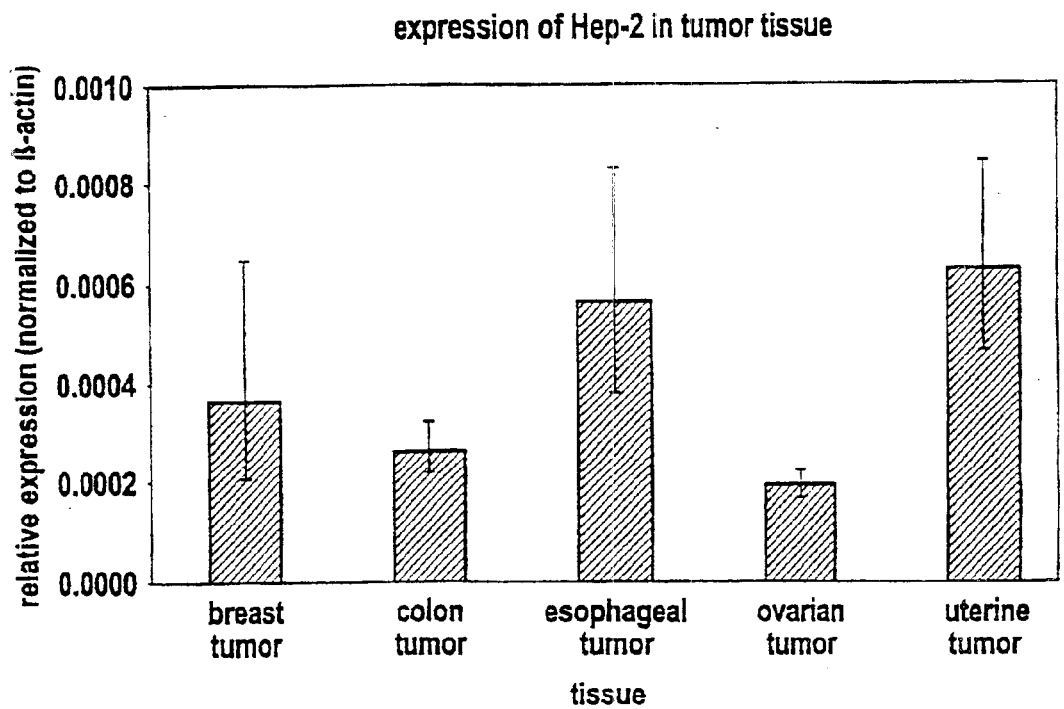
Figure 3:
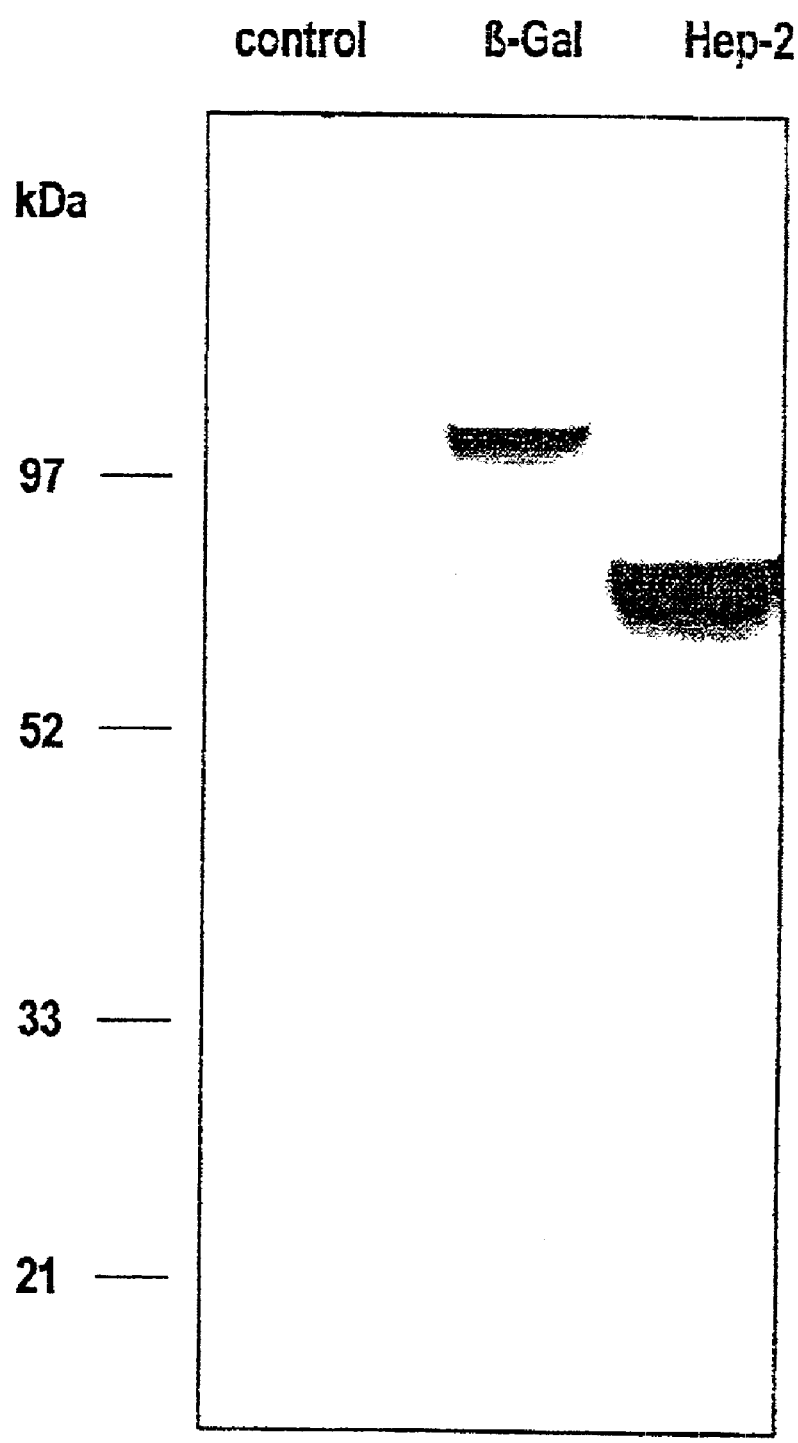

This invention relates to newly identified polypeptides and polynucleotides encoding such polypeptides sometimes hereinafter referred to as "heparanase-2", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to heparanase-2, in particular heparanase-2 polypeptides and heparanase-2 polynucleotides, recombinant materials and methods for their production. Such polypeptides and polynucleotides are of interest in relation to methods of treatment of certain diseases, including, but not limited to, autoimmune disorders, blood coagulation disorders, cancer, diabetes, ischemia, sepsis and stroke, cardiovascular diseases, thrombosis, hereinafter referred to as "diseases of the invention". In a further aspect, the invention relates to methods for identifying agonists and antagonists (e.g., inhibitors) using the materials provided by the invention, and treating conditions associated with heparanase-2 imbalance with the identified compounds. In a still further aspect, the invention relates to diagnostic assays for detecting diseases associated with inappropriate heparanase-2 activity or levels.

DESCRIPTION OF THE INVENTION

In a first aspect, the present invention relates to heparanase-2 polypeptides. Such polypeptides include:

(a) an isolated polypeptide encoded by a polynucleotide comprising the sequence of SEQ ID NO:1;

(b) an isolated polypeptide comprising a polypeptide sequence having at least 95%, 96%, 97%, 98%, or 99% identity to the polypeptide sequence of SEQ ID NO:2;

(c) an isolated polypeptide comprising the polypeptide sequence of SEQ ID NO:2;

(d) an isolated polypeptide having at least 95%, 96%, 97%, 98%, or 99% identity to the polypeptide sequence of SEQ ID NO:2;

(e) the polypeptide sequence of SEQ ID NO:2; and (f) an isolated polypeptide having or comprising a polypeptide sequence that has an Identity Index of 0.95, 0.96, 0.97, 0.98, or 0.99 compared to the polypeptide sequence of SEQ ID NO:2;

(g) fragments and variants of such polypeptides in (a) to (f).

Polypeptides of the present invention are believed to be members of the endoglucuronidase family of polypeptides. Heparan sulfate proteoglycans (HSPGS) are ubiquitous macromolecules of cell surfaces, basement membranes and the extracellular matrix (ECM). They play a major role in cell-ell and cell-extracellular matrix interactions. HSPGs have been reported to bind to a variety of different molecules like growth factors (e.g. fibroblast growth factors and platelet-derived growth factor), cytokines (e.g. interleukin-2), extracellular matrix proteins (e.g. fibronectin, laminin, collagen), factors involved in blood coagulation (e.g. antithrombin III), and other proteins such as lipoproteins, DNA topoisomerases, and □-amyloid proteins (Kjellen, L. and Lindahl, U., Annu. Rev. Biochem. 60, 443–475 (1991); Wight, T. N. et al., Curr. Opin. Cell Biol. 4, 793–801 (1992)).

Binding of signalling molecules to HSPGs leads to their sequestration, thereby creating a localised, readily accessible depot of these bound molecules, which can easily be released upon degradation of HSPGs (Nissen, N. et al., Biochem. J. 338, 637–642 (1999)). Additionally HSPGs are important structural components of the ECM. In capillaries they are found mainly in the subendothelial basement membrane, where they support the vascular endothelium and stabilise the structure of the capillary wall. Expression of heparan sulfate (HS)-degrading endoglucuronidases, commonly called "heparanases" (Nakajima, M. et al., J. Biol. Chem. 259, 2283–2290 (1984)), is found in blood borne cells and placental trophoblasts, reflecting their requirement for cell diapedesis activity associated with inflammatory processes or wound healing, and pregnancy, respectively (Vlodavsky, I. et al., invasion Metastasis 12, 112–127 (1992), Goshen, R. et al., Mol. Hum. Reprod. 2, 679–684 (1996)).

Degradation of the HS moieties of HSPGs affects a great variety of biological processes. Of particular interest is the proposed function of heparanases in neoangiogenesis and metastasis, associated with malignant tumours. It has been shown that secreted heparanase activity induces endothelial mitogenesis (Folkman, J. et al., Am. J. Pathol. 13, 393–400 (1988); Ishai-Michaeli, R. et al., Cell. Regul. 1, 833–842 (1990)) and is directly correlating with the metastatic property of a number of human metastatic cell lines as well as specimens of human breast, colon and river carcinomas (Nakajima, M. et al., Science 220, 611–613 (1983), Vlodavsky, I. et al., Cancer Res. 43, 2704β2711 (1983)).

Biochemical experiments identified so far three distinct groups of heparanase activities, with molecular weights of 137 kDa (Oosta, HG. M. et al., J. Biol. Chem. 257, 11249–11255 (1982)), 50 kDa (Freeman, C. and Parish, C. R., Biochem. J. 330, 1341–13509 (1998)), and 32–40 kDa (Hoogewerf, A. J. et al., J. Biol. Chem. 270, 3265–3277 (1995)). The first mammalian heparanase gene representing the 50 kDa class (Vlodavsky, I. et al., Nat. Medicine 5, 793–802 (1999); Hulett, M. D. et al., Nat. Medicine 5, 803–809 (1999); Toyoshina M. and Nakajima M., J. Biol. Chem. 270, 24153–24160 (1999)). The heparanase gene is preferentially expressed in highly metastatic mouse and human cell lines and in biopsy specimen of human tumours. Moreover, increased levels of heparanase were detected in sera (Nakajima, M. et al., Science 220, 611≧613, (1983)) and urine of metastatic tumour-bearing animals and cancer patients (Vlodavsky, I. et al., Nat. Medicine 5, 793–802

(1999)). Transfection of low or non-metastatic tumour cell lines with the heparanase gene confers a high metastatic potential in experimental mice, resulting in an increased rate of mortality. On the contrary, treatment of experimental animals with heparanase inhibitors (e.g., non-anticoagulant species of low-molecular-weight heparin and polysulfated saccharides) considerably reduces the incidence of lung metastases by melanoma, Lewis lung carcinoma and mammary adenocarcinoma cells (Vlodavsky I. et al., Invasion Metastasis 14, 290–302 (1995), Parish, C. R. et al., Int. J. Cancer 40, 511–517 (1987)). As it is generally accepted that heparanase activity plays a crucial role in many distinct biological processes, there is a clear need to identify further members of this protein family The biological properties of the heparanase-2 are hereinafter referred to as "biological activity of heparanase-2" or "heparanase-2 activity". Preferably, a polypeptide of the present invention exhibits at least one biological activity of heparanase-2.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments tat mediate the biological activity of heparanase-2, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains seretory or leader sequences, presequences, sequences that aid in purification, for instance multiple histidine residues, or an additional sequence for stability during recombinant production.

Polypeptides of the present invention can be prepared in any suitable manner, for instance by isolation form naturally occuring sources, from genetically engineered host cells comprising expression systems (vide infra) or by chemical synthesis, using for instance automated peptide synthesisers, or a combination of such methods. Means for preparing such polypeptides are well understood in the art.

In a further aspect, the present invention relates to heparanase-2 polynudeotides. Such polynucleotides include:

(a) an isolated polynucleotide comprising a polynucleotide sequence having at least 95%, 96%, 97%, 98%, or 99% identity to the polynucleotide sequence of SEQ ID NO:1;

(b) an isolated polynucleotide comprising the polynucleotide of SEQ ID NO:1;

(c) an isolated polynucleotide having at least 95%, 96%, 97%, 98%, or 99% identity to the polynucleotide of SEQ ID NO:1;

(d) the isolated polynucleotide of SEQ ID NO:1;

(e) an isolated polynucleotide comprising a polynucleotide sequence encoding a polypeptide sequence having at least 95%, 96%, 97%, 98%, or 99% identity to the polypeptide sequence of SEQ ID NO:2;

(f) an isolated polynucleotide comprising a polynucleotide sequence encoding the polypeptide of SEQ ID NO:2;

(g) an isolated polynucleotide having a polynucleotide sequence encoding a polypeptide sequence having at least 95%, 96%, 97%, 98%, or 99% identity to the polypeptide sequence of SEQ ID NO:2:

(h) an isolated polynucleotide encoding the polypeptide of SEQ ID NO:2;

(i) an isolated polynucleotide having or comprising a polynucleotide sequence that has an Identity Index of 0.95, 0.96, 0.97, 0.98, or 0.99 compared to the polynucleotide sequence of SEQ ID NO:1;

(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynudeotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;

(b) is the RNA transcript of the DNA sequence encoding the polypeptide of SEQ ID NO:2;

(c) comprises an RNA transcript of the DNA sequence of SEQ ID NO:1; or (d) is the RNA transcript of the DNA sequence of SEQ ID NO:1; and RNA polynucleotides that are complementary thereto.

The polynucleotide sequence of SEQ ID NO:1 shows homology with AF144325 (Vlodavsky, I. et al., Nat. Medicine 5, 793–802(1999)). The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2. The polypeptide of the SEQ ID NO:2 is related to other proteins of the endoglucuronidase family, having homology an/or structural similarity with AAD42342 (Vlodavsky, I. et al., Nat. Medicine 5, 793–802(1999)).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one heparanase-2 activity.

Polynucleotides of the present invention may be obtained using standard cloning and screening techniques from a cDNA library derived from mRNA in cells of human bladder, (see for instance, Sambrook et al., Molecular to Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gent et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific aligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated tansfection, transvection, microinjection, catonic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila S2* and *Spodoptera Sf9* cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacterophage genetic elements, such as cosmids and phagemids. The expression systems may contain control regions that regulate as well as engender expression. Generally, any system or vector that is able to maintain, propagate or express a polynucleotide to produce a polypeptide, in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or caton exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intercellular synthesis, isolation and/or purification.

Polynucleotides of the present invention may be used as diagnostic reagents, through detecting mutations in the associated gene. Detection of a mutated form of the gene characterised by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subjects cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may a be used in similar fashion. Deletions and insertions can be detected by a change in size of the amplified product in comparison to the normal genotype. Point mutations can be identified by hybridizing amplified DNA to labeled heparanase-2 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., *Science* (1985) 230:1242). Sequence changes at specific locations may also be revealed by nuclease protection assays, such as RNase and S1 protection or the chemical cleavage method (see Cotton et al, Proc Natl Acad Sci USA (1985) 85: 4397–4401).

An array of oligonucleotides probes comprising heparanase-2 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit comprising:
 (a) a polynucleotide of the present invention, preferably the nucleotide sequence of SEQ ID NO: 1, or a fragment or an RNA transcript thereof;
 (b) a nucleotide sequence complementary to that of (a);
 (c) a polypeptide of the present invention, preferably the polypeptide of SEQ ID NO:2 or a fragment thereof; or
 (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar; 5(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridisation techniques to clones arrayed on a grid, such as cDNA microarray hybridisation (Schena et al, Science, 270, 467–470, 1995 and Shalon et al, Genome Res, 6, 639–445, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in blood cells, cancer tissues, fetal liver, lymph nodes, placenta, spleen, trophoblast cells.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the to polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coggan et al., Current Protocols in Immunology 1(2):Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a heparanase-2 activity in the mixture, and comparing the heparanase-2 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and heparanase-2 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and heparanase-2 gene. The art of constructing transgenic animals is well established. For example, the heparanase-2 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knockout" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention.

Screening kits for use in the above described methods form a further aspect of the present invention. Such screening kits comprise:

(a) a polypeptide of the present invention;

(b) a recombinant cell expressing a polypeptide of the present invention;

(c) a cell membrane expressing a polypeptide of the present invention; or (d) an antibody to a polypeptide of the present invention; which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid sidechains and the amino or carboxyl termini. It vial be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substiutions include Gly, Ala; Val, lie, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylaton, ADP ribosylation and the like. Embodiments include methylation of the N-terminal amino acid, phosphorylations of serines and threonines and modification of C-terminal glycines.

"Allele" refers to one of two or more alternative forms of a gene occuring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of in unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448, 1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies *mutatis mutandis* for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between, the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-heparanase-2, employing an immunoglobulin Fc region as a part of a fusion protein is advantageous for performing the functional expression of Fc-heparanase-2 or fragments of heparanase-2, to improve pharmacokinetic properties of such a fusion protein when used for therapy and to generate a dimeric heparanase-2. The Fc-heparanase-2 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding heparanase-2 or fragments thereof. In some uses it would be desirable to be able to after the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Figures

FIG. 1

Quantification of the relative in vivo expression of (Heparanase-2) Hep-2 using a real-time quantitative reverse transcription-polymerase chain reaction (Taq-Man).

FIG. 2

Hep-2 is expressed in various tumor tissue. A real-time quantitative reverse transcription-polymerase chain reaction was used to quantify the relative expression of Heparanase-2 (normalized to β-actin).

FIG. 3

Expression of Heparanase-2 (Hep-2) in 293 human kidney fibroblastys.

Western blot analysis using anti-V5-HRP antibodies. Lane1 (control), cell lysate of 293 cells transiently transfected with pcDNA3/TRAF-His; lane 2 (β-gal), cell lysate of 293 cells transiently transfected with pcDNA3.1/lacZ-V5-His; lane 3 (Hep-2), cell lysate of 293 cells transiently transfected with pcDNA3.1/Hep-2-V5His.

FURTHER EXAMPLES

Example 1

RT-PCR in vivo expression has been evaluate using real-time quantitative reverse transcription-polymerase chain reaction (RT-PCR). As RT-PCR assay the Taq-Man fluorescence methodology (ABI PRISM 7700 Sequence detection system) was used. To quantify the relative expression of Heparanase-2 the upstream primer 5'-CCGATTCC-TATGCTGCAGGA-3' and the downstream primer 5'-TCACGACATCAATGCCCTGA-3' and the fluorescence-labeled probe (6-carboxyfluorescein, 6-carboxy-tetramethyl-rhodamine);

5'CTTATGGTTGAACACTTTAGGAATGCTGGCC-3' have been used. All reactions were done in a 96 well-plate with 40 PCR-cycles (according ABI PRISM 7700 SDS). Typical used PCR-cycles:1× 50° C. 2 min, 1× 95° C. 10 min, 40× 95° C. and 15 sec 60° C. 1 min.

The relative mRNA-expression was normalized to □-actin using the upstream primer 5'-ATTGCCGAC-AGGATGCAGAA-3', the downstream primer 5'-TTCCAGCAGATGTGGATCAGC-3' and the fluorescence-labeled probe (6-carboxyfluorescein, 6-carboxy-tetramethylrhodamine) 5'-CAAGATCATTGCT-CCTCCTGAGCGCA-3'.

RNA and cDNA were obtained from Analytical Biological Services Inc. (aorta, bone marrow, colon, corpus C., lymph node, ovary, spinal cord; stomach), Clontech, Heidelberg, (brain, heart, kidney, skeletal muscle, testis, uterus, prostate, pancreas, liver) and Invitrogen, Netherland, (tumor tissue).

Example 2

Cloning and Expression of Heparanase-2

The cDNA was generated from total prostate RNA (Clontech, Heidelberg) according to the SMART race cDNA amplification kit (#K1811-1, Clontech). Heparanase-2 DNA was amplified from the cDNA by the polymerase chain reaction (PCR) using the upstream primer1 5'-GCGAGACCCAGTAGGAAGAGAGG-3' and the downstream primer1 5'CAGCAGGCCCACTGGT-AGCCAT-3'.

Typical PCR-cycles: 5 cycles 94° C. 5 sec, 72° C. 3 min, 5 cycles 94° C. 5 sec, 70° C. 10 sec, 72° C. 3 min, 20 cycles 94° C. 5 sec, 68° C. 10 sec, 72 ° C. 3 min.

The PCR-product was further amplified using the upstream primer2 5'-ATGAGGGTGCTTTGTGCCTTCCC-3' and the downstream primer3 5'-TCGGTAGCGGCA- GGCCAAAGCA-3' according to the SMART race cDNA amplification kit (#K1811-1, Clontech). Typical PCR-cycles: 25 cycles 94° C. 5 sec, 68° C. 10 sec, 72° C. 3 min.

The PCR fragment was cloned into pcDNA3.1/V5His TOPO TA vector (# K4800-01, Invitrogen), sequenced using the BigDye-Kit (Applied Biosystems, Weiterstadt; ABI Prism 310 Genetic Analyzer) and used to transfect human 293 cells (ATCC, Rockville, Md.) with the SuperFect transfection reagent (#301305, Quiagen) according to the protocol for transient transfection of adherent cells (Quiagen). After 24 h cells were lysed for 15 min in lysis buffer (50 mM Tris pH 7,5; 10% NP40, 0,15% Deoxycholat, 1 mM EDTA, 1 µg/ml Aprotenin und Leupeptin, 1 mM PMSF), centrifuged for 10 min at 20000×g and loaded on a Novex Mini-Gel (#EI0001, Invitrogen). After transfer on Nitrocellulose (X cel blot module #EI9051, Invitrogen) the expressed Hep-2-V5-His fusion protein was detected using an anti-V5HRP antibody (#R961-25, Invitrogen). A vector containing LacZ-V5-His (Invitrogen) and a pcDNA3/His vector containing TRAF (Acc.No. Q13077) were used as controls.

Example 3

Production of Heparanase-2

Cells expressing Heparanase with a C-terminal histidin tag were lysed in lysis buffer (20 mM Tris pH 7,5; 150 mM NaCl, 1% TX-100, 0,25% NP40, 0,15% Deoxycholat, 1 µg/ml Aprotenin, 1 µg/ml Leupeptin, 1 mM PMSF). The expressed protein was purified using chelators such as NTA or imido acetic acid immobilized on a column matrix and modified with metal ions such as Co, Ni, or Cu. The expressed protein was detected by western blotting method using anti-His6 antibody (Quiagen/Invitrogen).

Example 4

Heparanase-2 Activity

Heparanase activity can be measured toward fluorescein isothiocyanate (FITC)-heparan sulfate (HS). One milligrams of heparane sulfate (Sigma) and 1 mg of FITC (Molecular probes, Oregon) were dissolved in 200 µl of 0,1 M sodium carbonate buffer, pH 9,5, and stirred overnight at 4° C. The solution was then futher loaded on a PD-10 desalting column (Pharmacia) to isolate FITC-HS. The cell lysate (example2) was added to the reaction mixture (50 mM sodium acetate, pH 4,2 containing FITC-HS) and incubated for 18 h at 37° C. The reaction was stopped by the addition of Heparin (Sigma). The products of FITC-HS yielded by this reaction were analyzed by gel chromatography (Amersham Pharmacia).

Example 5

Production of Heparanase-2 Specific Antibodies

Heparanase-2 purified using PAGE electrophoresis (Laemmli, 1970) is used to immunize rabbits for the production of antibodies using standard protocols.

The amino acid sequence translated from Hep-2 is analyzed using DNAStar software (DNAStar Inc) to determine regions of high immunogenicity. Synthetic peptides have been synthesized (amino-acid sequence 156–169 (VALDK QKGCK IAQH), 249–262 (ASKKY NISWE LGNE), 505–518(HRSRK KIKLA GTLR)) and used to raise antibodies using standard protocols.

The oligopeptides are 15 residues in length, and coupled to keyhole limpet hemocyanin (KLH, Sigma) by reaction with M-maleimidobenzoyl-N-hydroxysuccinimide ester (MBS, Pierce). Rabbits are immunized with the oligopeptide-KLH complex in complete Freud's adjuvant. The resulting antisera are tested for antipeptide activity, for example, by binding the peptide to nitrocellulose, blocking with 1% BSA, reacting with rabbit antisera, washing, and reacting with goat anti-rabbit-HRP (Biorad). High titered immune sera generated with the recombinant protein or synthetic peptide have been used to established ELISA technology and Western blot technique to monitor and quantitate the recombinant protein. Generally antibodies of a given specificity have been pooled and precipitated with Ammonium-sulfate and dialysed against PBS. Selected sera have been biotinylated using the NHS-ester derivative of the biotin, available via Pierce. Biotinylation was performed according to the manufacturer. The antigens and the immunochemical techniques used to rise and characterize the polyclonal antibodies can easily be extended with protocols used for the production of monoclonal antibody specificities. The expert in this field would make his choice between a to classical technique such as the hybridoma based technology or an antibody library based method according to his individual possibilities.

Example 6

Immuno-Assays for Estimation of Heparanase-2

Specific sera raised with recombinant heparanase-2 have been used as a "catcher antibody" for the coating of 96-well micro-titer plates (Nunc). 100 ml of the anti-Heparanase-2 serum (20 µg/ml) has been used to coate plates over night. Prior to use, the plates have been washed three times with PBS and have been incubated for one hour with a BSA solution (1%) in order to prevent unspecific binding. Surplus of blocking solution has been removed and 100 µl of Heparanase-2 has been added in serial delutions and has been incubated for one hour. Plates have been washed three times prior to the application of the biotinylated anti-Heparanase-2 antibody for detection. After one hour, readout has been performed via streptavidin-POD colour reaction with substrates such as ODB-tablets (Dako) measured at 490 nm.

What is claimed is:

1. An isolated polypeptide which is:
   (a) an isolated polypeptide encoded by a polynucleotide comprising the sequence of SEQ ID NO:1;
   (b) an isolated polypeptide comprising a polypeptide sequence having at least 95% identity to the polypeptide sequence of SEQ ID NO:2; or
   (c) an isolated polypeptide having at least 95% identity to the polypeptide sequence of SEQ ID NO:2 wherein said polypeptide has heparanase activity.

2. An isolated polypeptide comprising the polypeptide sequence of SEQ ID NO:2.

3. An isolated polypeptide which is the polypeptide sequence of SEQ ID NO:2.

4. An isolated polynucleotide which is:
   (a) an isolated polynucleotide comprising a polynucleotide sequence having at least 95% identity to the polynucleotide sequence of SEQ ID NO:1 and which hybridizes to SEQ ID NO 1 under stringent conditions comprising at 42° C. in a solution comprising 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C.;
   (b) an isolated polynucleotide having at least 95% identity to the polynucleotide of SEQ ID NO:1 and which hybridizes to SEQ ID NO 1 under stringent conditions comprising at 42° C. in a solution comprising 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C.;
   (c) an isolated polynucleotide comprising a polynucleotide sequence encoding a polypeptide sequence having at least 95% identity to the polypeptide sequence of SEQ ID NO:2;
   (d) an isolated polynucleotide having a polynucleotide sequence encoding a polypeptide sequence having at least 95% identity to the polypeptide sequence of SEQ ID NO:2;
   (e) an isolated polynucleotide with a nucleotide sequence of at least 100 nucleotides obtained by screening a library under stringent hybridization conditions 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. with a labeled probe having the sequence of SEQ ID NO: 1 or a fragment thereof having at least 15 nucleotides;
   (f) a polynucleotide which is the RNA equivalent of a polynucleotide of (a) to (e); or a polynucleotide sequence complementary over the entire length to said isolated polynucleotide of (a)–(f) wherein said polynucleotide encodes a polypeptide having heparanase activity.

5. An isolated polynucleotide which is:
   (a) an isolated polynucleotide comprising the polynucleotide of SEQ ID NO:1;
   (b) the isolated polynucleotide of SEQ ID NO:1;
   (c) an isolated polynucleotide comprising a polynucleotide sequence encoding the polypeptide of SEQ ID NO:2; or
   (d) an isolated polynucleotide encoding the polypeptide of SEQ ID NO:2.

6. An expression vector comprising a polynucleotide capable of producing a polypeptide of claim 1 when said expression vector is present in a compatible host cell.

7. A recombinant host cell comprising the expression vector of claim 6.

8. A fusion protein consisting of the Immunoglobulin Fc-region and a polypeptide of claim 1 wherein said fusion protein continues to have heparanase activity.

9. A method for screening to identify compounds that stimulate or inhibit the function or level of the polypeptide of claim 1 comprising a method selected from the group consisting of:
   (a) measuring or, detecting, quantitatively or qualitatively, the binding of a candidate compound to the polypeptide (or to the cells or membranes expressing the polypeptide) or a fusion protein thereof by means of a label directly or indirectly associated with the candidate compound;
   (b) measuring the competition of binding of a candidate compound to the polypeptide (or to the cells or membranes expressing the polypeptide) or a fusion protein thereof in the presence of a labeled competitior;
   (c) testing whether the candidate compound results in a signal generated by activation or inhibition of the polypeptide, using detection systems appropriate to the cells or cell membranes expressing the polypeptide;
   (d) mixing a candidate compound with a solution containing a polypeptide of claim 1, to form a mixture, measuring activity of the polypeptide in the mixture, and comparing the activity of the mixture to a control mixture which contains no candidate compound; or
   (e) detecting the effect of a candidate compound on the production of mRNA encoding said polypeptide or said polypeptide in cells, using for instance, an ELISA assay, and
   (f) producing said compound according to biotechnological or chemical standard techniques.

10. An isolated polypeptide of claim 1, wherein said polypeptide is encoded by a polynucleotide sequence which hybridizes to SEQ ID NO 1 under stringent conditions comprising at 42° C. in a solution comprising 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C.

11. An isolated polypeptide of claim 2, which is encoded by a polynucleotide sequence of SEQ ID NO:1.

12. A process for producing a heparanase polypeptide, comprising:
   culturing a host cell comprising a polynucleotide of claim 4, and an expression control region to regulate expression of said polynucleotide, under conditions suitable for the production of said polypeptide.

13. A process for producing a heparanase polypeptide, comprising:
   culturing a host cell comprising a polynucleotide of claim 5, and an expression control region to regulate expression of said polynucleotide, under conditions suitable for the production of said polypeptide.

14. A process for producing a heparanase polypeptide, comprising:
   culturing a host cell comprising an expression vector comprising a polynucleotide encoding a polypeptide of claim 1, which is capable of producing said polypeptide, under conditions suitable for production of said polypeptide.

15. A process for producing a heparanase polypeptide, comprising:
   culturing a host cell comprising an expression vector comprising a polynucleotide encoding a polypeptide of claim 2, which is capable of producing said polypeptide, under conditions suitable for production of said polypeptide.

16. A process for producing a heparanase polypeptide, comprising:
   culturing a host cell comprising an expression vector comprising a polynucleotide encoding a polypeptide of claim 3, which is capable of producing said polypeptide, under conditions suitable for production of said polypeptide.

* * * * *

SEQUENCE LISTING

```
<160> NUMBER OF SEQ ID NOS: 15

<210> SEQ ID NO 1
<211> LENGTH: 1779
<212> TYPE: DNA
<213> ORGANISM: Homo sapiens
<220> FEATURE:
<221> NAME/KEY: CDS
<222> LOCATION: (1)..(1779)

<400> SEQUENCE: 1
```

-continued

```
atg agg gtg ctt tgt gcc ttc cct gaa gcc atg ccc tcc agc aac tcc     48
Met Arg Val Leu Cys Ala Phe Pro Glu Ala Met Pro Ser Ser Asn Ser
 1               5                  10                  15 cgc ccc ccc gcg tgc cta gcc ccg ggg gct ctc tac ttg gct ctg ttg     96
Arg Pro Pro Ala Cys Leu Ala Pro Gly Ala Leu Tyr Leu Ala Leu Leu
             20                  25                  30 ctc cat ctc tcc ctt tcc tcc cag gct gga gac agg aga ccc ttg cct    144
Leu His Leu Ser Leu Ser Ser Gln Ala Gly Asp Arg Arg Pro Leu Pro
         35                  40                  45 gta gac aga gct gca ggt ttg aag gaa aag acc ctg att cta ctt gat    192
Val Asp Arg Ala Ala Gly Leu Lys Glu Lys Thr Leu Ile Leu Leu Asp
 50                  55                  60 gtg agc acc aag aac cca gtc agg aca gtc aat gag aac ttc ctc tct    240
Val Ser Thr Lys Asn Pro Val Arg Thr Val Asn Glu Asn Phe Leu Ser
 65                  70                  75                  80 ctg cag ctg gat ccg tcc atc att cat gat ggc tgg ctc gat ttc cta    288
Leu Gln Leu Asp Pro Ser Ile Ile His Asp Gly Trp Leu Asp Phe Leu
                 85                  90                  95 agc tcc aag cgc ttg gtg acc ctg gcc cgg gga ctt tcg ccc gcc ttt    336
Ser Ser Lys Arg Leu Val Thr Leu Ala Arg Gly Leu Ser Pro Ala Phe
            100                 105                 110 ctg cgc ttc ggg ggc aaa agg acc gac ttc ctg cag ttc cag aac ctg    384
Leu Arg Phe Gly Gly Lys Arg Thr Asp Phe Leu Gln Phe Gln Asn Leu
        115                 120                 125 agg aac ccg gcg aaa agc cgc ggg ggc ccg ggc ccg gat tac tat ctc    432
Arg Asn Pro Ala Lys Ser Arg Gly Gly Pro Gly Pro Asp Tyr Tyr Leu
    130                 135                 140 aaa aac tat gag gat gac att gtt cga agt gat gtt gcc tta gat aaa    480
Lys Asn Tyr Glu Asp Asp Ile Val Arg Ser Asp Val Ala Leu Asp Lys
145                 150                 155                 160 cag aaa ggc tgc aag att gcc cag cac cct gat gtt atg ctg gtg ctc    528
Gln Lys Gly Cys Lys Ile Ala Gln His Pro Asp Val Met Leu Val Leu
                165                 170                 175 caa agg gag aag gca gct cag atg cat ctg gtt ctt cta aag gag caa    576
Gln Arg Glu Lys Ala Ala Gln Met His Leu Val Leu Leu Lys Glu Gln
            180                 185                 190 ttc tcc aat act tac agt aat ctc ata tta aca gcc agg tct cta gac    624
Phe Ser Asn Thr Tyr Ser Asn Leu Ile Leu Thr Ala Arg Ser Leu Asp
        195                 200                 205 aaa ctt tat aac ttt gct gat tgc tct gga ctc cac ctg ata ttt gct    672
Lys Leu Tyr Asn Phe Ala Asp Cys Ser Gly Leu His Leu Ile Phe Ala
    210                 215                 220 cta aat gca ctg cgt cgt aat ccc aat aac tcc tgg aac agt tct agt    720
Leu Asn Ala Leu Arg Arg Asn Pro Asn Asn Ser Trp Asn Ser Ser Ser
225                 230                 235                 240 gcc ctg agt ctg ttg aag tac agc gcc agc aaa aag tac aac att tct    768
Ala Leu Ser Leu Leu Lys Tyr Ser Ala Ser Lys Lys Tyr Asn Ile Ser
                245                 250                 255 tgg gaa ctg ggt aat gag cca aat aac tat cgg acc atg cat ggc cgg    816
Trp Glu Leu Gly Asn Glu Pro Asn Asn Tyr Arg Thr Met His Gly Arg
            260                 265                 270 gca gta aat ggc agc cag ttg gga aag gat tac atc cag ctg aag agc    864
Ala Val Asn Gly Ser Gln Leu Gly Lys Asp Tyr Ile Gln Leu Lys Ser
        275                 280                 285 ctg ttg cag ccc atc cgg att tat tcc aga gcc agc tta tat ggc cct    912
Leu Leu Gln Pro Ile Arg Ile Tyr Ser Arg Ala Ser Leu Tyr Gly Pro
    290                 295                 300 aat att ggg cgg ccg agg aag aat gtc atc gcc ctc cta gat gga ttc    960
Asn Ile Gly Arg Pro Arg Lys Asn Val Ile Ala Leu Leu Asp Gly Phe
305                 310                 315                 320
```

```
atg aag gtg gca gga agt aca gta gat gca gtt acc tgg caa cat tgc         1008
Met Lys Val Ala Gly Ser Thr Val Asp Ala Val Thr Trp Gln His Cys
            325                 330                 335 tac att gat ggc cgg gtg gtc aag gtg atg gac ttc ctg aaa act cgc         1056
Tyr Ile Asp Gly Arg Val Val Lys Val Met Asp Phe Leu Lys Thr Arg
        340                 345                 350 ctg tta gac aca ctc tct gac cag att agg aaa att cag aaa gtg gtt         1104
Leu Leu Asp Thr Leu Ser Asp Gln Ile Arg Lys Ile Gln Lys Val Val
            355                 360                 365 aat aca tac act cca gga aag aag att tgg ctt gaa ggt gtg gtg acc         1152
Asn Thr Tyr Thr Pro Gly Lys Lys Ile Trp Leu Glu Gly Val Val Thr
370                 375                 380 acc tca gct gga ggc aca aac aat cta tcc gat tcc tat gct gca gga         1200
Thr Ser Ala Gly Gly Thr Asn Asn Leu Ser Asp Ser Tyr Ala Ala Gly
385                 390                 395                 400 ttc tta tgg ttg aac act tta gga atg ctg gcc aat cag ggc att gat         1248
Phe Leu Trp Leu Asn Thr Leu Gly Met Leu Ala Asn Gln Gly Ile Asp
                405                 410                 415 gtc gtg ata cgg cac tca ttt ttt gac cat gga tac aat cac ctc gtg         1296
Val Val Ile Arg His Ser Phe Phe Asp His Gly Tyr Asn His Leu Val
            420                 425                 430 gac cag aat ttt aac cca tta cca gac tac tgg ctc tct ctc ctc tac         1344
Asp Gln Asn Phe Asn Pro Leu Pro Asp Tyr Trp Leu Ser Leu Leu Tyr
        435                 440                 445 aag cgc ctg atc ggc ccc aaa gtc ttg gct gtg cat gtg gct ggg ctc         1392
Lys Arg Leu Ile Gly Pro Lys Val Leu Ala Val His Val Ala Gly Leu
450                 455                 460 cag cgg aag cca cgg cct ggc cga gtg atc cgg gac aaa cta agg att         1440
Gln Arg Lys Pro Arg Pro Gly Arg Val Ile Arg Asp Lys Leu Arg Ile
465                 470                 475                 480 tat gct cac tgc aca aac cac cac aac cac aac tac gtt cgt ggg tcc         1488
Tyr Ala His Cys Thr Asn His His Asn His Asn Tyr Val Arg Gly Ser
                485                 490                 495 att aca ctt ttt atc atc aac ttg cat cga tca aga aag aaa atc aag         1536
Ile Thr Leu Phe Ile Ile Asn Leu His Arg Ser Arg Lys Lys Ile Lys
            500                 505                 510 ctg gct ggg act ctc aga gac aag ctg gtt cac cag tac ctg ctg cag         1584
Leu Ala Gly Thr Leu Arg Asp Lys Leu Val His Gln Tyr Leu Leu Gln
        515                 520                 525 ccc tat ggg cag gag ggc cta aag tcc aag tca gtg caa ctg aat ggc         1632
Pro Tyr Gly Gln Glu Gly Leu Lys Ser Lys Ser Val Gln Leu Asn Gly
530                 535                 540 cag ccc tta gtg atg gtg gac gac ggg acc ctc cca gaa ttg aag ccc         1680
Gln Pro Leu Val Met Val Asp Asp Gly Thr Leu Pro Glu Leu Lys Pro
545                 550                 555                 560 cgc ccc ctt cgg gcc ggc cgg aca ttg gtc atc cct cca gtc acc atg         1728
Arg Pro Leu Arg Ala Gly Arg Thr Leu Val Ile Pro Pro Val Thr Met
                565                 570                 575 ggc ttt tat gtg gtc aag aat gtc aat gct ttg gcc tgc cgc tac cga         1776
Gly Phe Tyr Val Val Lys Asn Val Asn Ala Leu Ala Cys Arg Tyr Arg
            580                 585                 590 taa                                                                      1779

<210> SEQ ID NO 2
<211> LENGTH: 592
<212> TYPE: PRT
<213> ORGANISM: Homo sapiens

<400> SEQUENCE: 2
```

```
Met Arg Val Leu Cys Ala Phe Pro Glu Ala Met Pro Ser Ser Asn Ser
 1               5                  10                  15

Arg Pro Pro Ala Cys Leu Ala Pro Gly Ala Leu Tyr Leu Ala Leu Leu
                20                  25                  30

Leu His Leu Ser Leu Ser Ser Gln Ala Gly Asp Arg Arg Pro Leu Pro
            35                  40                  45

Val Asp Arg Ala Ala Gly Leu Lys Glu Lys Thr Leu Ile Leu Leu Asp
        50                  55                  60

Val Ser Thr Lys Asn Pro Val Arg Thr Val Asn Glu Asn Phe Leu Ser
 65              70                  75                  80

Leu Gln Leu Asp Pro Ser Ile Ile His Asp Gly Trp Leu Asp Phe Leu
                85                  90                  95

Ser Ser Lys Arg Leu Val Thr Leu Ala Arg Gly Leu Ser Pro Ala Phe
            100                 105                 110

Leu Arg Phe Gly Gly Lys Arg Thr Asp Phe Leu Gln Phe Gln Asn Leu
        115                 120                 125

Arg Asn Pro Ala Lys Ser Arg Gly Gly Pro Gly Pro Asp Tyr Tyr Leu
    130                 135                 140

Lys Asn Tyr Glu Asp Asp Ile Val Arg Ser Asp Val Ala Leu Asp Lys
145                 150                 155                 160

Gln Lys Gly Cys Lys Ile Ala Gln His Pro Asp Val Met Leu Val Leu
                165                 170                 175

Gln Arg Glu Lys Ala Ala Gln Met His Leu Val Leu Leu Lys Glu Gln
            180                 185                 190

Phe Ser Asn Thr Tyr Ser Asn Leu Ile Leu Thr Ala Arg Ser Leu Asp
        195                 200                 205

Lys Leu Tyr Asn Phe Ala Asp Cys Ser Gly Leu His Leu Ile Phe Ala
    210                 215                 220

Leu Asn Ala Leu Arg Arg Asn Pro Asn Asn Ser Trp Asn Ser Ser Ser
225                 230                 235                 240

Ala Leu Ser Leu Leu Lys Tyr Ser Ala Ser Lys Tyr Asn Ile Ser
                245                 250                 255

Trp Glu Leu Gly Asn Glu Pro Asn Asn Tyr Arg Thr Met His Gly Arg
            260                 265                 270

Ala Val Asn Gly Ser Gln Leu Gly Lys Asp Tyr Ile Gln Leu Lys Ser
        275                 280                 285

Leu Leu Gln Pro Ile Arg Ile Tyr Ser Arg Ala Ser Leu Tyr Gly Pro
    290                 295                 300

Asn Ile Gly Arg Pro Arg Lys Asn Val Ile Ala Leu Leu Asp Gly Phe
305                 310                 315                 320

Met Lys Val Ala Gly Ser Thr Val Asp Ala Val Thr Trp Gln His Cys
                325                 330                 335

Tyr Ile Asp Gly Arg Val Val Lys Val Met Asp Phe Leu Lys Thr Arg
            340                 345                 350

Leu Leu Asp Thr Leu Ser Asp Gln Ile Arg Lys Ile Gln Lys Val Val
        355                 360                 365

Asn Thr Tyr Thr Pro Gly Lys Lys Ile Trp Leu Glu Gly Val Val Thr
    370                 375                 380

Thr Ser Ala Gly Gly Thr Asn Asn Leu Ser Asp Ser Tyr Ala Ala Gly
385                 390                 395                 400

Phe Leu Trp Leu Asn Thr Leu Gly Met Leu Ala Asn Gln Gly Ile Asp
                405                 410                 415

Val Val Ile Arg His Ser Phe Phe Asp His Gly Tyr Asn His Leu Val
```

```
                420             425             430
Asp Gln Asn Phe Asn Pro Leu Pro Asp Tyr Trp Leu Ser Leu Leu Tyr
            435                 440                 445
Lys Arg Leu Ile Gly Pro Lys Val Leu Ala Val His Val Ala Gly Leu
    450                 455                 460
Gln Arg Lys Pro Arg Pro Gly Arg Val Ile Arg Asp Lys Leu Arg Ile
465                 470                 475                 480
Tyr Ala His Cys Thr Asn His His Asn His Asn Tyr Val Arg Gly Ser
                485                 490                 495
Ile Thr Leu Phe Ile Ile Asn Leu His Arg Ser Arg Lys Lys Ile Lys
            500                 505                 510
Leu Ala Gly Thr Leu Arg Asp Lys Leu Val His Gln Tyr Leu Leu Gln
            515                 520                 525
Pro Tyr Gly Gln Glu Gly Leu Lys Ser Lys Ser Val Gln Leu Asn Gly
            530                 535                 540
Gln Pro Leu Val Met Val Asp Asp Gly Thr Leu Pro Glu Leu Lys Pro
545                 550                 555                 560
Arg Pro Leu Arg Ala Gly Arg Thr Leu Val Ile Pro Pro Val Thr Met
                565                 570                 575
Gly Phe Tyr Val Val Lys Asn Val Asn Ala Leu Ala Cys Arg Tyr Arg
            580                 585                 590

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: RT PCR
      Primer1

<400> SEQUENCE: 3
ccgattccta tgctgcagga                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: RT PCR
      Primer2

<400> SEQUENCE: 4
tcacgacatc aatgccctga                                             20

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Labeled
      probe1

<400> SEQUENCE: 5
cttatggttg aacactttag gaatgctggc c                                31

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: PT PCR
      Primer3
```

```
<400> SEQUENCE: 6
attgccgaca ggatgcagaa                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: RT PCR
      Primer4

<400> SEQUENCE: 7
ttccagcaga tgtggatcag c                                                  21

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Labeled
      Probe2

<400> SEQUENCE: 8
caagatcatt gctcctcctg agcgca                                             26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Upstream
      Primer5

<400> SEQUENCE: 9
gcgagaccca gtaggaagag agg                                                23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Downstream
      Primer6

<400> SEQUENCE: 10
cagcaggccc actggtagcc at                                                 22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Upstream
      Primer7

<400> SEQUENCE: 11
atgagggtgc tttgtgcctt ccc                                                23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Downstream
      Primer8
```

-continued

```
<400> SEQUENCE: 12
tcggtagcgg caggccaaag ca                                              22

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Peptide 1

<400> SEQUENCE: 13

Val Ala Leu Asp Lys Gln Lys Gly Cys Lys Ile Ala Gln His
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Peptide 2

<400> SEQUENCE: 14

Ala Ser Lys Lys Tyr Asn Ile Ser Trp Glu Leu Gly Asn Glu
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Peptide 3

<400> SEQUENCE: 15

His Arg Ser Arg Lys Lys Ile Lys Leu Ala Gly Thr Leu Arg
 1               5                  10
```